US00PP11309P

United States Patent [19]

Plevier

[11] Patent Number: Plant 11,309

[45] Date of Patent: Mar. 21, 2000

[54] ALSTROEMERIA PLANT NAMED 'MAGIC LOVE'

[75] Inventor: F. B. Plevier, Sassenheim, Netherlands

[73] Assignee: Koninklijke Van Zanten B.V., Hillegom, Netherlands

[21] Appl. No.: 09/106,646

[22] Filed: Jun. 29, 1998

[51] Int. Cl.[7] ..... A01H 5/00

[52] U.S. Cl. ..... Plt./309

[58] Field of Search ..... Plt./309

[56] References Cited

PUBLICATIONS

UPOV–ROM, 1999/02, Plant Variety Database, GTI Jouve Retrieval Software, citations (2) for 'Magic Love'.

*Primary Examiner*—Howard J. Locker
*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria which is a cross of two unnamed, undistributed seedlings. The varietal denomination of the new variety is 'Magic Love'.

The first act of asexual reproduction of 'Magic Love' was in Rijsenhout, The Netherlands, by tissue culture. Asexual reproduction by tissue culture through successive generations in Rijsenhout, The Netherlands, has demonstrated that the combination of characteristics as herein disclosed for 'Magic Love' are firmly fixed and retained through successive generations.

SUMMARY OF THE INVENTION

The new variety of Alstroemeria, 'Magic Love', produces large red purple flowers.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Rijsenhout, The Netherlands in the month of April. Color designations indicated are in accordance with The Royal Horticultural Society Color Chart by color plate designations.

'Magic Love' has not been observed under all possible environmental conditions. Phenotypic expression may vary with variations in environment such as temperature, light intensity, day length and growing and cultural conditions.

Botanical classification:

*Family.*—Amaryllidaceae.

*Genus.*—Alstroemeria sp. Commercial: Alstroemeria hybrid.

Origin: Seedling.

Plant:

*Form.*—Bushy, short upright growing stems.

*Growth.*—Vigorous.

*Height.*—About 15 to 30 cm.

*Branching.*—No branching until umbel, stems arise from Rhizomes.

*Flower stem.*—Length: About 15 to 30 cm. Color: Near 143C.

*Foliage.*—Quantity: Few, about 8 to 15 per stem. Size of leaf: About 2 to 8 cm long, about 0.5 to 2 cm wide. Shape of leaf: Oblong, lanceolate shape. Margin: Egal. Texture: Upper side and underside leathery. Color: Upper side near 137A; underside near 137C. Venation: Linear. Stem color: Near 143C. Rhizomes: Average about 5 to 25 cm, near 155D.

*Peduncle.*—Length: About 4 to 7 cm. Color: Near 143C. Strength: Strong. Aspect: Erect.

Bud stage:

*Form.*—Ovoid.

*Size.*—About 5 to 6 cm long, about 1 to 2 cm diameter.

*Opening characteristics.*—Buds open from the lowermost part to the top.

*Color of tepals when beginning to unfurl.*—Near 61B.

Flower stage:

*Blooming habit.*—Continuous.

*Time of flowering.*—Spring, summer and autumn.

*Flower.*—Diameter: About 6 to 8 cm. Depth: About 5 to 7 cm. Borne: Upright, at a slight angle to perpendicular. Shape: Umbel, about 2 to 5 blooms. Color: Near 60C. Length: About 2 to 4 cm. Diameter: About 2 to 3 mm. Discoloration after full bloom: Slight. Hairy: No.

*Bloom.*—Form: Tubular. Tepalage: 6, obovate. Margin of tepals: Minutely crimped. Apex: Outside tepals rounded; inside tepals pointed. Persistence: Flowers fall off after maturity. Lasting quality: About 12 to 16 days after cutting, about 3 weeks on plant. Flower coloration: Uniformly colored outer tepals; inner tepals have the same color as outer tepals; inner tepals upper surface have yellowish/white base up to about ½ of tepal. Inner tepals: Near 60C and 155D with purplish brown stripes near 187A. Outer tepals: Near 60C. Point of tepal attachment: Green. Discoloration as bloom ages: Color becomes slightly more intense.

*Fragrance.*—Absent.

Reproductive organs:

*Stamens.*—About 6, near 82C. Arrangement: Side-by-side. Anthers: Near 152C. Filaments: Near 82C. Pollen: Yellow, not fertile.

*Pistils.*—1. Styles: Near 57D. Stigmas: Near 73C. Shape of fruit: Ovoid. Size: About 1 to 1.5 cm round.

I claim:

1. A new variety of Alstroemeria plant substantially as herein shown and described.

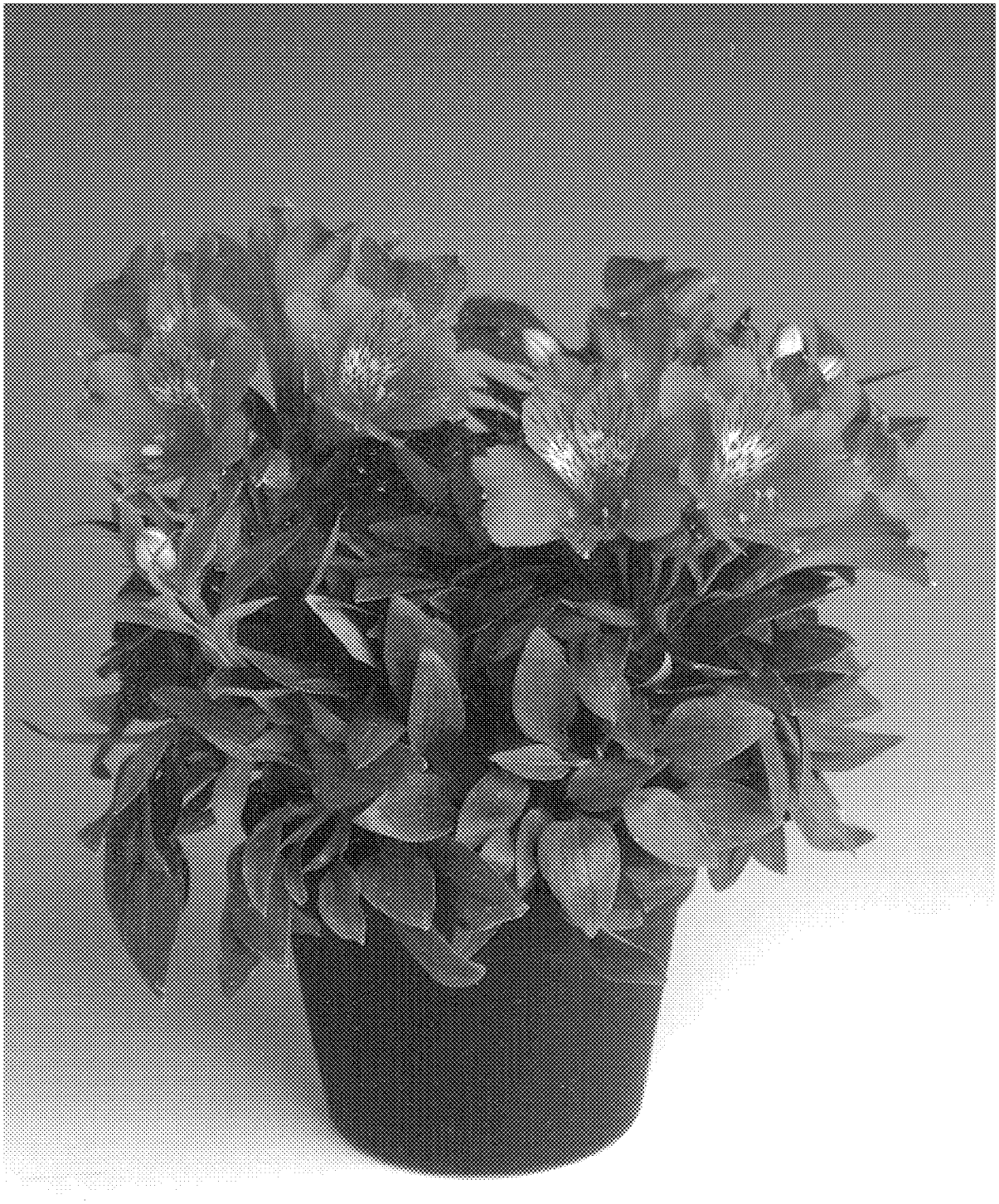

* * * * *